United States Patent [19]

Brockway

[11] Patent Number: 5,425,634
[45] Date of Patent: * Jun. 20, 1995

[54] APPARATUS FOR SUPPORTING AND CONTROLLING FLUID DELIVERY TO A DENTAL HANDPIECE

[75] Inventor: Charles E. Brockway, Fairview, N.C.

[73] Assignee: Knight Manufacturing, Inc., Asheville, N.C.

[*] Notice: The portion of the term of this patent subsequent to Feb. 9, 2010 has been disclaimed.

[21] Appl. No.: 196,392

[22] Filed: Feb. 15, 1994

Related U.S. Application Data

[63] Continuation-in-part of Ser. No. 136,452, Oct. 14, 1993.

[51] Int. Cl.⁶ ............................................. A61C 1/02
[52] U.S. Cl. .......................................... 433/28; 433/77
[58] Field of Search .................... 433/28, 77, 78, 80, 433/84

[56] References Cited

U.S. PATENT DOCUMENTS

| | | |
|---|---|---|
| 3,986,262 | 10/1976 | Casillas . |
| 4,117,861 | 10/1978 | Betush ............................ 137/595 |
| 4,231,737 | 11/1980 | Groen ............................. 433/78 |
| 4,375,963 | 3/1983 | Betush ............................ 433/28 |
| 5,145,366 | 9/1992 | Janhunen ........................ 433/77 |
| 5,158,453 | 10/1992 | Brockway ....................... 433/28 |

Primary Examiner—Cary E. O'Connor
Attorney, Agent, or Firm—Shefte, Pinckney & Sawyer

[57] ABSTRACT

An apparatus for supporting and controlling fluid delivery to a dental handpiece includes a frame with a holder for receiving the handpiece, a compressed air actuating arrangement having a valve which is opened and closed by the insertion and removal of the handpiece into and from the holder, and fluid delivery tubing which extends to the handpiece and is affixed at spaced locations to the frame and to the actuating arrangement for folding of the tubing upon itself to close the tubing against fluid flow when the handpiece is mounted in its holder and for unfolding the tubing for open fluid flow when the handpiece is removed from the holder.

9 Claims, 2 Drawing Sheets

APPARATUS FOR SUPPORTING AND CONTROLLING FLUID DELIVERY TO A DENTAL HANDPIECE

CROSS-REFERENCE TO RELATED APPLICATION

This is a continuation-in-part of U.S. patent application Ser. No. 08/136,452, filed Oct. 14, 1993, pending, entitled APPARATUS FOR SUPPORTING AND CONTROLLING FLUID DELIVERY TO A DENTAL HANDPIECE.

BACKGROUND OF THE INVENTION

The present invention relates generally to dental office equipment of the type commonly used in dentists' offices for routine patient procedures. More particularly, the present invention relates to a novel apparatus for supporting and controlling delivery of fluids, such as air and water, to a dental handpiece, such as a dentist's drill.

Currently, conventional equipment used by practicing dentists typically comprises a variety of hand-held power-operated tools for performing differing dental procedures, one of the most common and familiar of which, by way of example, is a drill used for removing decayed portions of teeth preparatory to filling with a protective material. Typically, such drills and like dental handpieces are driven by compressed air and it is also commonplace for a cooling fluid, usually air, water or a mixture thereof, to be delivered to the handpiece for emission into the drilling or other work area for cooling purposes.

To facilitate convenient usage of such handpieces by dentists, a conduit system is provided in the dentist's office to provide a ready source of compressed air and pressurized water and is equipped with an associated valving system, normally actuated and deactuated through a foot-operated device, to enable the dentist to selectively control fluid delivery to the dental handpieces being utilized.

In the past, such valving systems have been relatively complicated and, in turn, costly, not only to manufacture but also to service when in need of repair. Accordingly, a need has existed for a simplified and less costly form of valve system for controlling delivery of operating fluids to dental handpieces.

U.S. Pat. No. 4,375,963, represents a relatively recent development addressing this problem and need. Basically, this patent discloses a control unit for dental handpieces wherein a handpiece holder is carried on a pivoting support arm mounted to a suitable frame member. A resiliently flexible tube is attached to the handpiece and extends therefrom through the frame member in a configuration tending to urge the support arm into an upwardly pivoted position when the handpiece is removed from the holder. An actuator is mounted in a stationary position on the frame member adjacent the holder for engagement by the handpiece when inserted into the holder to cause the support arm to pivot into a downward position. In such position, opposing pinch members mounted on the frame member and the support arm are moved into sufficiently close proximity to one another to physically clamp the flexible tube between the pinch members and thereby close the tube to prevent further fluid flow to the handpiece. Upon subsequent removal of the handpiece from the holder, the natural resiliency of the tube urges the support arm into its upward disposition, thereby separating the pinch members to allow fluid flow through the tube.

SUMMARY OF THE INVENTION

It is an object of the present invention to provide an equally simplified apparatus for supporting and controlling delivery of an operating fluid for a dental handpiece which avoids the necessity of physically pinching fluid delivery tubing to accomplish opening and closing thereof, but rather operates to close and open the tubing by folding and unfolding, i.e., kinking and unkinking, the tubing without physically contacting the tubing at the fold location.

Briefly summarized, the apparatus of the present invention basically comprises a frame member having a holder mounted thereon for receiving the dental handpiece and an actuating arrangement for movement between a deactuating position when the dental handpiece is received by the holder and an actuating position when the dental handpiece is removed from the holder. Tubing is provided for delivering the operating fluid for the dental handpiece, the tubing being affixed at spaced locations therealong respectively to the frame member and to the actuating arrangement to define a fixed length of the tubing therebetween. When the actuator is in its deactuating position, the fixed length of the tubing is folded upon itself to prevent fluid flow through the tubing. When the actuator is in its actuating position, the tubing is sufficiently relaxed to permit fluid flow therethrough.

In the preferred embodiment, the actuating arrangement is arranged to move the spaced locations of affixation of the tubing toward and away from one another upon movement between the actuating and deactuating positions. In particular, the frame member rotatably supports a first tube connection pin and the actuating arrangement rotatably supports a second tube connection pin, with the tubing being affixed to the tube connection pins in diametrical relation thereto at the spaced locations along the tubing for unitary rotational movement of the tube connection pins and the tubing upon movement of the actuating arrangement.

Preferably, the actuating arrangement includes an actuating arm pivotably mounted to the frame member and an appropriate device or means associated with the holder for pivoting the actuating arm between the actuating and deactuating positions. In the preferred embodiment, a linear actuator is arranged in engagement with the actuating arm for linear movement between a first position when the dental handpiece is received by the holder and a second position when the dental handpiece is removed from the holder. A source of compressed air is connected to the linear actuator for operation thereof and a valve assembly is associated with the holder for movement between a closed position blocking delivery of the compressed air to the linear actuator when the handpiece is removed from the holder and an open position permitting delivery of compressed air to the linear actuator when the handpiece is received in the holder. One preferred form of linear actuator is a piston-and-cylinder assembly equipped with a return spring or other device for biasing the assembly into its second position.

DETAILED DESCRIPTION OF THE PREFERRED EMBODIMENT

Figure 1:
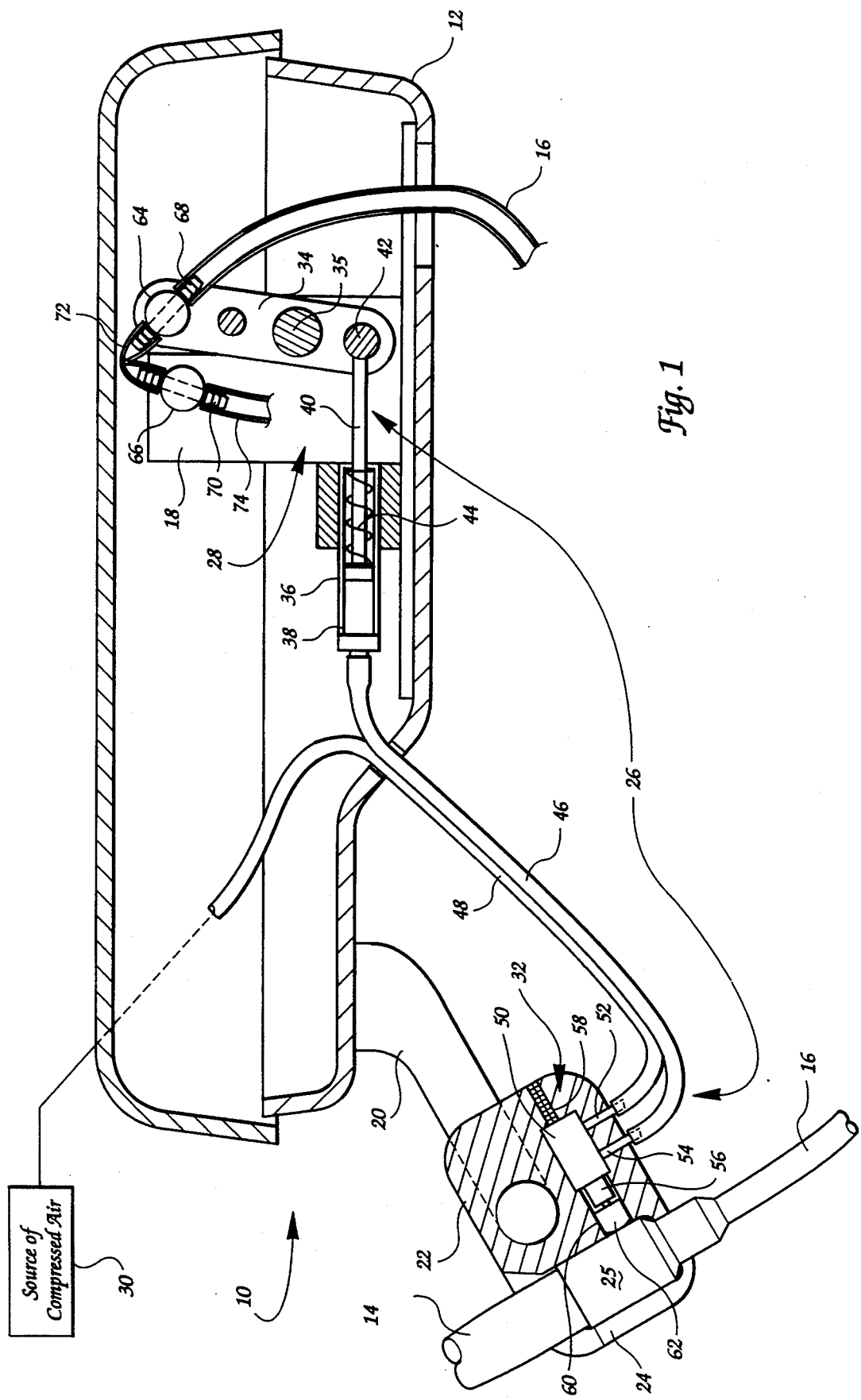
FIG. 1 is a side elevational view, partially in vertical cross-section, of a dental handpiece supporting and controlling apparatus according to a preferred embodiment of the present invention, showing the dental handpiece received in its holder, the actuating arrangement in its deactuating position, and the tubing folded upon itself to prevent fluid flow therethrough.

Referring now to the accompanying drawings, a dental handpiece supporting and controlling apparatus unit in accordance with the preferred embodiment of the present invention is shown generally at 10. As those persons skilled in the art will recognize and understand, a plurality of the apparatus units 10 will typically be contained within the same frame or housing 12 in side-by-side relation, with each apparatus unit 10 being connected to an individual respective dental handpiece 14, e.g., a dental drill, to control delivery of operating fluids, e.g., pressurized air and water, to the respective handpiece 14 through appropriate tubing 16. The frame 12 thereby serves as an instrument head and is typically mounted on an articulated support linkage (not shown) in association with a conventional dental chair (also not shown).

The apparatus 10 of the present invention is particularly adapted for use with conventional dental handpieces of the type designed to be powered by pressurized air and also supplied with a pressurized cooling fluid such as water, air or both. However, those persons skilled in the art will readily recognize that the apparatus of the present invention is equally applicable for supporting and controlling any other form of dental handpiece wherein at least one operating fluid is to be selectively supplied to the handpiece during use.

A handpiece support arm 20 is rigidly affixed to the underside of the main frame 12 and extends downwardly and forwardly therefrom. The distal end of the support arm 20 carries a handpiece holder 22 configured in the form of a saddle defining a forwardly opening channel 24 for selective insertion and removal of the handpiece 14 into and out of the channel 24. To facilitate a secure fitted receipt of the handpiece 14 within the channel 24 of the saddle-shaped holder 22, the base of the handpiece 14 is fitted with an adaptor nut 25 whose outer peripheral shape conforms closely to the interior dimensions and configuration of the holder channel 24.

An actuating arrangement, generally indicated collectively at 26, includes an actuating linkage 28 mounted within the main frame 12 and operated by a source of compressed air, indicated only representatively at 30, under the control of a pilot valve arrangement 32 mounted within the handpiece holder 22.

The actuating linkage 28 includes an actuating arm 34 pivotably supported within the frame 12 on a subframe 18 for pivoting movement generally within a vertical plane about a horizontal axis 35. A linear actuator 36, preferably in the form of a fluid-actuated piston-and-cylinder assembly, has its cylindrical housing 38 rigidly mounted to the subframe 18 with its piston 40 extending rearwardly into engagement with an actuating pin 42 affixed to the lower end of the pivot arm 34 beneath the pivot axis 35, for horizontal extending and retracting movement of the piston 40 in a linear path of movement to actuate pivoting movement of the arm 34. The linear actuator 36 includes a biasing spring 44 disposed within the cylindrical housing 38 to urge the piston 40 into a normally retracted position withdrawn into the cylinder 38. The opposite end of the cylinder 38 is connected to a compressed air supply tube 46 which, in turn, is connected through the pilot valve assembly 32 and through another compressed air supply tube 48 with the compressed air source 30 for actuating extension of the piston 40 from the cylinder housing 38.

The pilot valve assembly 32 includes a valve housing 50 having inlet and outlet ports 52, 54 respectively connected to the compressed air supply tubes 48, 46. A valve control member 56 is slidably supported by the valve housing 50 for linear movement between a valve-closing position blocking compressed air communication between the inlet and outlet ports 52, 54, when the valve member 56 is extended forwardly from the housing 50 and a valve-opening position permitting compressed air communication between the inlet and outlet ports 52, 54, when the valve member 56 is withdrawn into the housing 50. A biasing spring (not shown) is disposed within the valve housing 50 to normally urge the valve member 56 into its valve-closing position. An adjusting screw 58 is provided in the handpiece holder 22 to permit, as necessary, adjustment of the relative disposition of the biasing spring and the valve member 56 within the housing 50. The valve member 56 extends outwardly from the valve housing 50 within a bore 60 opening into the channel 24 of the handpiece holder 22. An actuator button 62 is affixed to the distal end of the valve member 56 to extend into the channel 24 when the handpiece 14 is removed, whereby the valve member 56 assumes its normal valve-closing disposition under the biasing force of its associated spring, and to be engaged and depressed by the adaptor nut 25 when the handpiece 14 is received by the holder 22, whereby the valve member 56 is retracted into its valve-opening disposition.

The pivot arm 34 carries a pin 64 for rotational movement upon pivotal movement of the arm 34 in parallel relation to its pivot axis. A corresponding pin 66 is similarly mounted rotatably to the subframe 18 at a fixed disposition adjacent and in parallel relation to the pin 64. Each of the pins 64, 66 is formed with a diametrical bore, each bore receiving a respective tubular fitting 68, 70 secured therein to project outwardly from each opposite side of the respective pin 64, 66. The fittings 68, 70 are communicated with one another by a segment of a relatively flexible tube 72. The opposite end of the fitting 70 is connected to a supply tube 74 which extends from the apparatus 10 through its articulated support linkage to a suitable source of fluid supply (not shown). The opposite end of the fitting 68 is connected to the tubing 16 extending to the handpiece 14.

As will be understood, although the drawings only show a single continuous line of tubing to the handpiece 14, the pins 64, 66 may support several corresponding pairs of fittings to accommodate the supply of differing respective pressurized fluids to the associated handpiece 14, e.g., to be usable with conventional dental handpieces powered by pressurized air and also supplied with a pressurized cooling fluid (water, air or both) such as a conventional dental drill wherein the exposed drill bit is operatively connected interiorly with a turbine configured to be rotatably driven by a supply of compressed air with separate supplies of coolant water and air also being delivered for emission from the drill at the drilling location for cooling purposes.

Normal operation of the handpiece supporting and controlling apparatus 10 of the present invention may thus be understood. When the handpiece 14 is rested in its holder 22 on the frame 12, the button actuator 62 of the valve arrangement 32 is depressed by the adaptor nut 25 of the handpiece 14, moving the valve control member 56 into its valve-opening position so that compressed air from the source 30 is supplied through the tubes 48, 46 to the linear actuator 36, causing its piston 40 to be extended and, in turn, to pivot the arm 34 counterclockwise (as viewed in the drawings) into the upright disposition shown in FIG. 1. In this disposition of the actuating arrangement 26, the tube connection pin 64 supported by the arm 34 is held in sufficiently close proximity to the tube connection pin 66 on the subframe 18 to cause the tube segment 72 to become folded upon itself into a crimped or kinked configuration sufficient to block fluid flow through the tube segment 72. Thus, with the handpiece 14 supported within the holder 22, fluid flow through the tube system of the apparatus 10 is prevented.

Figure 2:
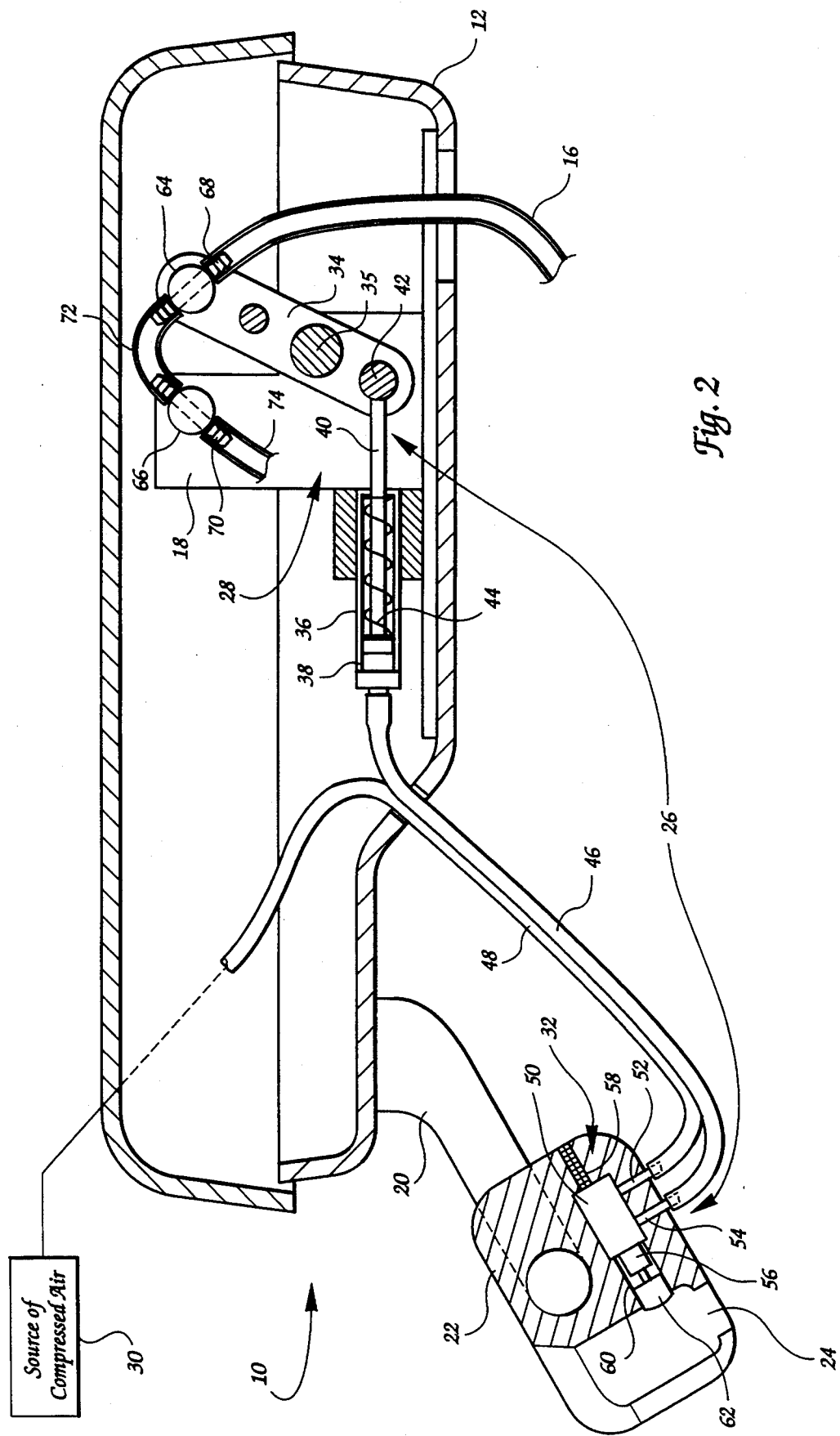
FIG. 2 is another side elevational view similar to FIG. 1, showing the dental handpiece removed from its holder, the actuating arrangement in its actuating position, and the tubing relaxed to permit fluid flow.

Upon removal of the handpiece 14 from the holder 22, e.g., to extend the handpiece 14 to a patient, the actuator button 62 is thereby released to extend into the channel 24 under the biasing force of the spring within the valve housing 50, permitting the valve control member 56 to assume its normal valve-closing disposition preventing compressed air flow to the linear actuator 36. In this disposition, the outlet port 54 of the valve assembly 32 is vented to the atmosphere allowing compressed air captured within the supply tube 46 and the cylinder 38 to escape. In turn, the biasing spring 44 of the linear actuator 36 operates to retract the piston 40 into its normally withdrawn position. In the absence of a pivoting force operating on the actuating pin 42 of the pivot arm 34, the natural resilient tendency of the flexible tube segment 72 to relax itself acts through the fittings 68, 70, and their supporting pins 64, 66, to pivot the arm 34 and its tube connection pin 64 away from the subframe 18 and its tube connection pin 66 into the inclined disposition of the arm 34 shown in FIG. 2, sufficiently to permit fluid flow through the tube segment 72. Thus, upon actuation by the dentist of the associated foot-operated control with the handpiece supporting and controlling apparatus in this open position, pressurized operating fluid, e.g., air, water or both, is permitted to flow through the tubing system to the handpiece 14 for normal operation thereof.

Those persons skilled in the art will readily recognize that the dental handpiece supporting and controlling apparatus 10 of the present invention is of a simplified construction which is relatively inexpensive to produce and furthermore should operate reliably over a relatively extended useful life.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. Apparatus for supporting and controlling delivery of operating fluid for a dental handpiece, said apparatus comprising a frame member having a holder mounted thereon for receiving the dental handpiece, actuator means for movement between a deactuating position when the dental handpiece is received by said holder and an actuating position when the dental handpiece is removed from said holder, and tube means for delivering an operating fluid for the dental handpiece, said tube means being affixed at spaced locations therealong respectively to said frame member and to said actuator means to define a fixed length of said tube means therebetween, said fixed length of said tube means being folded upon itself to prevent fluid flow therethrough when said actuator means is in its deactuating position and being sufficiently relaxed to permit fluid flow therethrough when said actuator means is in its actuating position.

2. Apparatus for supporting and controlling fluid delivery to a dental handpiece according to claim 1, wherein said actuator means is arranged to move said spaced locations of affixation of said tube means toward and away from one another upon movement between said actuating and deactuating positions.

3. Apparatus for supporting and controlling fluid delivery to a dental handpiece according to claim 2, wherein said frame member rotatably supports a first tube connection pin and said actuator means rotatably supports a second tube connection pin, said tube means being affixed to said tube connection pins in diametrical relation thereto at said spaced locations along said tube means for unitary rotational movement of said tube connection pins and said tube means upon movement of said actuator means.

4. Apparatus for supporting and controlling fluid delivery to a dental handpiece according to claim 1, wherein said actuator means comprises an actuating arm pivotably mounted to said frame member and means associated with said holder for pivoting said actuating arm between said actuating and deactuating positions.

5. Apparatus for supporting and controlling fluid delivery to a dental handpiece according to claim 4, wherein said tube means is affixed at one said spaced location to said actuating arm.

6. Apparatus for supporting and controlling fluid delivery to a dental handpiece according to claim 4, wherein said means for pivoting said actuating arm comprises a linear actuator arranged for engagement with said actuating arm and means associated with said holder for actuating linear movement of said linear actuator between a first position when the dental handpiece is received by said holder and a second position when the dental handpiece is removed from said holder.

7. Apparatus for supporting and controlling fluid delivery to a dental handpiece according to claim 6, wherein said means for actuating linear movement of said linear actuator comprises a source of compressed air connected to said linear actuator and valve means associated with said holder for movement between a closed position blocking delivery of compressed air to said linear actuator when the handpiece is removed from said holder and an open position permitting delivery of compressed air to said linear actuator when the handpiece is received in said holder.

8. Apparatus for supporting and controlling fluid delivery to a dental handpiece according to claim 6, wherein said linear actuator comprises a piston-and-cylinder assembly.

9. Apparatus for supporting and controlling fluid delivery to a dental handpiece according to claim 6, wherein said linear actuator includes means biasing the linear actuator into its said second position.

* * * * *